(12) United States Patent
Lazarus

(10) Patent No.: US 9,604,033 B2
(45) Date of Patent: Mar. 28, 2017

(54) BODY CAVITY DRAINAGE DEVICES WITH LOCKING DEVICES AND RELATED METHODS

(71) Applicant: Harrison M. Lazarus, Salt Lake City, UT (US)

(72) Inventor: Harrison M. Lazarus, Salt Lake City, UT (US)

(73) Assignee: Harrison M. Lazarus, Salt Lake City, UT (US)

( * ) Notice: Subject to any disclaimer, the term of this patent is extended or adjusted under 35 U.S.C. 154(b) by 307 days.

(21) Appl. No.: 14/318,550

(22) Filed: Jun. 27, 2014

(65) Prior Publication Data

US 2015/0374959 A1    Dec. 31, 2015

(51) Int. Cl.
*A61M 27/00*    (2006.01)
*A61M 25/00*    (2006.01)
(Continued)

(52) U.S. Cl.
CPC ......... *A61M 25/0136* (2013.01); *A61M 1/008* (2013.01); *A61M 25/007* (2013.01);
(Continued)

(58) Field of Classification Search
CPC .......... A61M 1/008; A61M 2025/0019; A61M 2025/0081; A61M 25/007; A61M 25/0102;
(Continued)

(56) References Cited

U.S. PATENT DOCUMENTS 2,393,002 A    1/1946 Smith
2,898,917 A    8/1959 Wallace
(Continued)

FOREIGN PATENT DOCUMENTS

RU    2012371 C1    5/1994
RU    2415682 C1    4/2011
(Continued)

OTHER PUBLICATIONS

Ben-Isaac et al., "Flexible Fiberoptic Pleuroscopy: Pleural and Lung Biopsy*," Experimental Approaches, Chest Journal No. 67, <http://journal.publications.chestnet.org/data/Journals/CHEST/20966/573.pdf>, May 5, 1975, pp. 573-576.
(Continued)

*Primary Examiner* — Adam Marcetich
(74) *Attorney, Agent, or Firm* — TraskBritt

(57) ABSTRACT

A body cavity drainage device includes a drainage tube having a proximal end, a distal end, and one or more lumens extending longitudinally through a wall thereof. The distal end may be configured to be inserted into a body cavity of a patient during use of the body cavity drainage device. An activation apparatus is configured to alter a position of the distal end of the drainage tube relative to the proximal end of the drainage tube. The activation apparatus may include a rotatable control device and one or more flexible members disposed within the one or more lumens extending longitudinally through a wall of the drainage tube. The one or more flexible members may be operably coupled to the rotatable control device and to the drainage tube. Methods relate to forming and using a body cavity drainage device.

19 Claims, 8 Drawing Sheets

(51) Int. Cl.
*A61M 25/01* (2006.01)
*B65H 75/44* (2006.01)
*A61M 1/00* (2006.01)

(52) U.S. Cl.
CPC ..... *A61M 25/0102* (2013.01); *A61M 25/0147* (2013.01); *A61M 2025/0019* (2013.01); *A61M 2025/0081* (2013.01); *A61M 2207/00* (2013.01); *B65H 75/4431* (2013.01); *B65H 2701/36* (2013.01); *B65H 2701/537* (2013.01)

(58) Field of Classification Search
CPC .......... A61M 25/0113; A61M 25/0136; A61M 25/0147; A61M 27/00; A61M 25/0133; A61M 25/0105; A61M 2025/015; A61B 2034/301; A61B 2017/003; A61B 2017/00318; A61B 2017/00323; A61B 2017/00327; B65H 75/4431; B65H 2701/537; B65H 2701/34; B65H 2701/35; B65H 2701/36; B65H 2701/37; A43C 11/165; Y10T 24/2187; Y10T 74/1967; Y10T 403/32262; H02G 11/02; A45F 5/004; G01B 2003/101
See application file for complete search history.

(56) References Cited

U.S. PATENT DOCUMENTS

| | | | |
|---|---|---|---|
| 3,225,762 A | | 12/1965 | Guttman |
| 3,416,532 A | | 12/1968 | Grossman |
| 3,610,231 A | | 10/1971 | Takahashi et al. |
| 3,683,929 A | | 8/1972 | Holter |
| 3,830,238 A | | 8/1974 | Kurtz et al. |
| 3,863,641 A | | 2/1975 | Popa |
| 3,937,418 A | * | 2/1976 | Critelli ............... B65H 75/4431 119/796 |
| 3,943,929 A | | 3/1976 | Patel |
| 4,068,383 A | * | 1/1978 | Krebs ................ G01B 3/1005 242/385.4 |
| 4,105,031 A | | 8/1978 | Kurtz et al. |
| 4,202,510 A | * | 5/1980 | Stanish ............. B65H 75/4431 242/384.7 |
| 4,203,430 A | | 5/1980 | Takahashi |
| 4,228,802 A | | 10/1980 | Trott et al. |
| 4,439,189 A | | 3/1984 | Sargeant et al. |
| 4,571,239 A | | 2/1986 | Heyman |
| 4,608,982 A | | 9/1986 | Pollard |
| 4,692,154 A | | 9/1987 | Singery et al. |
| 4,769,019 A | | 9/1988 | Kerwin |
| 4,862,891 A | | 9/1989 | Smith |
| 4,883,474 A | | 11/1989 | Sheridan et al. |
| 4,920,980 A | | 5/1990 | Jackowski |
| 5,026,358 A | | 6/1991 | Everett, Jr. et al. |
| 5,040,543 A | | 8/1991 | Badera et al. |
| 5,047,018 A | | 9/1991 | Gay et al. |
| 5,108,368 A | | 4/1992 | Hammerslag et al. |
| 5,141,503 A | | 8/1992 | Sewell |
| 5,157,813 A | * | 10/1992 | Carroll ..................... A43C 7/00 24/68 B |
| 5,205,830 A | | 4/1993 | Dassa et al. |
| 5,207,661 A | | 5/1993 | Repschlager |
| 5,297,310 A | | 3/1994 | Cox et al. |
| 5,300,050 A | | 4/1994 | Everett, Jr. et al. |
| 5,312,357 A | | 5/1994 | Buijs et al. |
| 5,364,351 A | | 11/1994 | Heinzelman et al. |
| 5,370,610 A | | 12/1994 | Reynolds et al. |
| 5,397,321 A | | 3/1995 | Houser et al. |
| 5,409,462 A | | 4/1995 | Ross |
| 5,409,468 A | | 4/1995 | Sachse |
| 5,456,664 A | * | 10/1995 | Heinzelman ...... A61M 25/0147 600/585 |
| 5,540,648 A | | 7/1996 | Yoon et al. |
| 5,601,087 A | | 2/1997 | Gunderson et al. |
| 5,616,131 A | | 4/1997 | Sauer et al. |
| 5,630,795 A | | 5/1997 | Kuramoto et al. |
| 5,653,696 A | | 8/1997 | Shiber et al. |
| 5,772,670 A | | 6/1998 | Brosa |
| 5,807,341 A | | 9/1998 | Heim |
| 5,895,400 A | | 4/1999 | Abela |
| 5,897,534 A | | 4/1999 | Heim et al. |
| 5,987,344 A | | 11/1999 | West et al. |
| 6,045,623 A | | 4/2000 | Cannon et al. |
| 6,171,277 B1 | * | 1/2001 | Ponzi ................. A61B 18/1492 604/22 |
| 6,183,450 B1 | | 2/2001 | Lois |
| 6,193,691 B1 | | 2/2001 | Beardsley |
| 6,254,581 B1 | | 7/2001 | Scott |
| 6,468,260 B1 | * | 10/2002 | Bumbalough .... A61M 25/0136 600/434 |
| 6,500,167 B1 | | 12/2002 | Webster |
| 6,514,273 B1 | | 2/2003 | Voss et al. |
| 6,530,913 B1 | | 3/2003 | Giba et al. |
| 6,530,935 B2 | | 3/2003 | Wensel et al. |
| 6,638,253 B2 | | 10/2003 | Breznock |
| 6,907,992 B2 | | 6/2005 | McMichael et al. |
| 7,037,290 B2 | | 5/2006 | Gardeski et al. |
| 7,407,128 B1 | * | 8/2008 | Chang ................ B65H 75/4431 242/385.4 |
| 7,497,854 B2 | | 3/2009 | Gill et al. |
| 7,578,814 B2 | | 8/2009 | Accisano, III et al. |
| 7,740,623 B2 | | 6/2010 | Nayak et al. |
| 7,758,586 B2 | | 7/2010 | Muto et al. |
| 8,220,460 B2 | | 7/2012 | Tanaka |
| 8,246,752 B2 | | 8/2012 | Boyle, Jr. |
| 8,388,759 B2 | | 3/2013 | Boyle, Jr. et al. |
| 8,409,070 B2 | | 4/2013 | Carol et al. |
| 2001/0005785 A1 | | 6/2001 | Sachse |
| 2001/0007922 A1 | | 7/2001 | Schwager |
| 2003/0208252 A1 | | 11/2003 | O' Boyle et al. |
| 2003/0225364 A1 | | 12/2003 | Kraft et al. |
| 2004/0035017 A1 | * | 2/2004 | Yang ................. B65H 75/4431 33/767 |
| 2004/0116852 A1 | | 6/2004 | Scopton |
| 2005/0184186 A1 | * | 8/2005 | Tsoi ................... B65H 75/4431 242/378.1 |
| 2005/0277875 A1 | | 12/2005 | Selkee |
| 2006/0142695 A1 | | 6/2006 | Knudson |
| 2006/0173449 A1 | | 8/2006 | Sharareh et al. |
| 2006/0264925 A1 | | 11/2006 | Sharareh et al. |
| 2006/0264988 A1 | | 11/2006 | Boyle |
| 2006/0280773 A1 | | 12/2006 | Roschak et al. |
| 2007/0016133 A1 | | 1/2007 | Pepper |
| 2007/0060997 A1 | | 3/2007 | de Boer |
| 2007/0078455 A1 | | 4/2007 | Rashidi |
| 2007/0156116 A1 | * | 7/2007 | Gonzalez ............ A61B 1/0052 604/528 |
| 2007/0167923 A1 | | 7/2007 | Deal |
| 2007/0287993 A1 | * | 12/2007 | Hinman ............. A61B 17/062 606/1 |
| 2008/0021415 A1 | | 1/2008 | Durkin et al. |
| 2008/0045921 A1 | | 2/2008 | Anderson et al. |
| 2008/0097293 A1 | | 4/2008 | Chin et al. |
| 2008/0236209 A1 | * | 10/2008 | Conti ................... E05B 45/005 70/18 |
| 2009/0005771 A1 | | 1/2009 | Lieber et al. |
| 2009/0012365 A1 | * | 1/2009 | Ueno ................... A61B 1/0052 600/146 |
| 2009/0062769 A1 | | 3/2009 | Graves et al. |
| 2009/0227900 A1 | | 9/2009 | Kim et al. |
| 2009/0270838 A1 | | 10/2009 | Berthiaume et al. |
| 2009/0299327 A1 | | 12/2009 | Tilson et al. |
| 2010/0101061 A1 | * | 4/2010 | Ha ....................... A43B 3/0042 24/712.5 |
| 2010/0137775 A1 | | 6/2010 | Hu et al. |
| 2010/0168731 A1 | | 7/2010 | Wu et al. |
| 2010/0191057 A1 | | 7/2010 | Jansen et al. |
| 2010/0222664 A1 | | 9/2010 | Lemon et al. |
| 2010/0249490 A1 | | 9/2010 | Farnan |
| 2010/0249520 A1 | | 9/2010 | Shelton, IV et al. |
| 2010/0264244 A1 | * | 10/2010 | Spencer ............... B65H 75/28 242/378 |

(56) References Cited

U.S. PATENT DOCUMENTS

| | | |
|---|---|---|
| 2011/0040285 A1 | 2/2011 | Boyle |
| 2011/0062268 A1* | 3/2011 | Cheng ................ B65H 75/4431 242/378.1 |
| 2011/0077498 A1 | 3/2011 | McDaniel |
| 2011/0213300 A1 | 9/2011 | McWeeney et al. |
| 2011/0224647 A1 | 9/2011 | Lazarus |
| 2011/0264089 A1 | 10/2011 | Zirkle et al. |
| 2011/0282153 A1* | 11/2011 | Ueki .................... A61B 1/0052 600/149 |
| 2012/0116161 A1 | 5/2012 | Nieman et al. |
| 2012/0157921 A1 | 6/2012 | Hoofnagle et al. |
| 2012/0172703 A1 | 7/2012 | Esguerra et al. |
| 2013/0023840 A1 | 1/2013 | Loske et al. |
| 2013/0046250 A1 | 2/2013 | Bode |
| 2013/0158379 A1 | 6/2013 | Selkee |
| 2013/0204087 A1 | 8/2013 | Jaworek et al. |
| 2013/0211385 A1 | 8/2013 | Lazarus |
| 2013/0276718 A1* | 10/2013 | Valadez ................ A01K 27/004 119/796 |
| 2013/0310767 A1 | 11/2013 | Solar et al. |
| 2014/0150782 A1 | 6/2014 | Vazales et al. |
| 2014/0193138 A1 | 7/2014 | Koren |
| 2014/0290014 A1* | 10/2014 | Myrick ................ A43C 11/165 24/712.2 |
| 2015/0148595 A1 | 5/2015 | Bagwell et al. |
| 2015/0374889 A1* | 12/2015 | Lazarus ............. A61B 17/3415 604/541 |
| 2015/0374959 A1 | 12/2015 | Lazarus |

FOREIGN PATENT DOCUMENTS

| | | |
|---|---|---|
| WO | 9325264 A1 | 12/1993 |
| WO | 9952481 A1 | 10/1999 |

OTHER PUBLICATIONS

"Catheter prevents clogging," Research & Development, <<http://www.rdmag.com/printpdf/award-winners/2011/08/catheter-prevents-clogging>>, Aug. 14, 2011, 3 pages.

"Express Dry Seal Chest Drain, Instructions for Use," Atrium, www.atriummed.com (2003) 2 pages.

"Medical pleuroscopy", <http://www.cancercenter.com/treatments/medical-pleuroscopy/>, Cancer Treatment Centers of America, retrieved Aug. 19, 2013, 2 Pages.

"Rocket® Cardiothoracic Range," Rocketmedical, Issue 1, R89947, Jan. 2011, 23 pages.

* cited by examiner

BODY CAVITY DRAINAGE DEVICES WITH LOCKING DEVICES AND RELATED METHODS

BACKGROUND

Field

Embodiments of the invention relate to body cavity drainage devices and related devices and methods.

State of the Art

Drainage devices, especially for the evacuation of a pleural cavity, may consist of a hollow flexible tube inserted through an incision into the pleural cavity. The shape and configuration of the pleural cavity often necessitates multiple incisions to be made to permit the drainage tube to reach various locations in the pleural cavity. The need for multiple incisions may generally result in an extended hospital stay for a patient suffering from a severe case of pleurisy.

BRIEF SUMMARY

In one embodiment of the disclosure, a body cavity drainage device for a patient includes a drainage tube having a proximal end, a distal end, and one or more lumens extending longitudinally through a wall thereof. The distal end may be configured to be inserted into a body cavity of a patient to facilitate use of the body cavity drainage device. The body cavity drainage device may also include an activation apparatus configured to alter a position of the distal end of the drainage tube relative to the proximal end of the drainage tube. The activation apparatus may include a rotatable control device, one or more flexible members disposed within the one or more lumens extending longitudinally through a wall of the drainage tube, the one or more flexible members operably coupled to the rotatable control device at a proximal end of the one or more flexible members and to the drainage tube at or near a distal end of the one or more flexible members, and a compliant locking mechanism configured to maintain an angular position of the rotatable control device when in a locked position and in the absence of a torque applied to the rotatable control device, and to allow rotation of the control device when in an unlocked position upon application of a torque to the rotatable control device.

In another embodiment of the disclosure, a body cavity drainage device for a patient may include a drainage tube having a proximal end and a distal end and an activation apparatus coupled to the proximal end of the drainage tube. The activation apparatus may include a pinion gear attached to a control device, at least one rack meshed with the pinion gear, at least one flexible member extending along a length of the drainage tube and coupled to the distal end of the drainage tube, the at least one flexible member attached to the at least one rack, and a compliant locking mechanism proximate the control device, the compliant locking mechanism comprising a locking lever and serrations configured to engage with gear teeth of the pinion gear when the locking lever is in a locked position.

In yet another embodiment of the disclosure, a method of forming a body cavity drainage device for a patient may include coupling an activation apparatus to a proximal end of a drainage tube, the activation apparatus configured to bend the drainage tube in response to a torque input at a rotatable control device of the activation apparatus, and engaging a locking mechanism with the rotatable control device to substantially prevent rotation of the rotatable control device in the absence of an applied torque to the rotatable control device.

In yet another embodiment of the disclosure, a method of draining fluid from a body cavity, comprising positioning a distal end of a tube of a body cavity drainage device at a first position within the body cavity, draining fluid from the body cavity through the distal end of the tube of the body cavity drainage device in the first position, depressing a locking lever to unlock a rotatable control device of the body cavity drainage device external to the body cavity, and moving the distal end of the tube of the body cavity drainage device to a second, different position within the body cavity. Moving the distal end of the tube of the body cavity drainage device to a second, different position within the body cavity may include rotating the rotatable control device of the body cavity drainage device, the rotatable control device coupled to the distal end of the tube of the body cavity drainage device by flexible members.

DETAILED DESCRIPTION

As used herein, the term "distal" relates to an end of a device configured to be inserted into the body cavity of a patient, and the term "proximal" relates to an end of a device configured to be outside of a patient.

In one embodiment of the present disclosure, a body cavity drainage device includes a body cavity drainage tube with a proximal end and a distal end. The proximal end of the body cavity drainage tube may be connected to an activation apparatus including a rotatable control device and a compliant locking mechanism. Rotation of the rotatable control device may cause the distal end of the body cavity drainage tube to move relative to the proximal end of the drainage tube. In an unlocked position, the compliant locking mechanism may allow rotation of the rotatable control device. In a locked position, the compliant locking mechanism may substantially prevent rotation of the rotatable control device until a predetermined torque value is applied to the rotatable control device.

In another embodiment of the present disclosure, a body cavity drainage device includes a body cavity drainage tube extending along a central axis between a proximal end and a distal end. A fluid outlet may be oriented substantially coaxially with the drainage tube. The proximal end of the body cavity drainage tube may be attached to an activation apparatus. The activation apparatus may include a rotatable control device for controlling a position of the distal end of the body cavity drainage tube.

In yet another embodiment of the present disclosure, a body cavity drainage device placement tool for use with a body cavity drainage tube includes a shaft, a handle at or near a proximal end of the shaft, and a distal end of the shaft for insertion through at least one lateral opening of the body cavity drainage tube and at least partially through a central lumen of the body cavity drainage tube for placement of the distal end of the body cavity drainage tube in a body cavity of a patient.

In yet another embodiment of the present disclosure, a package including at least three of a body cavity drainage device, a drainage tube placement tool, a drainage tube cleaning device, and a visualization device may be provided to a user.

Figure 1:
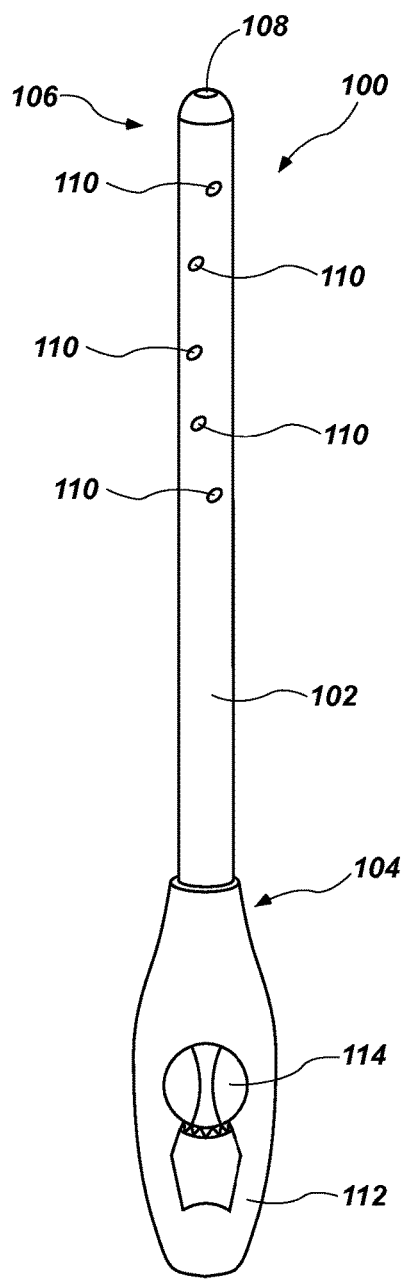
FIG. 1 shows a top view of a drainage device according to an embodiment of the present disclosure.

FIG. 1 shows a drainage device 100 according to an embodiment of the present disclosure. The drainage device 100 may include a drainage tube 102 configured to provide drainage to a body cavity defined by or surrounded by soft tissue. For example, the drainage device 100 may be used to withdraw infection exudates from a pleural cavity by applying suction to the drainage tube 102. In addition, positive pressure may be applied to the drainage tube 102, such as to introduce a fluid into the drainage tube 102 and/or body cavity, such as to dissolve material to be removed or to dislodge flow restrictions within the drainage tube 102.

Although the drainage device 100 is described herein relative to use with pleural cavities, the present disclosure is not so limited. Accordingly, the drainage device 100, elements thereof, and accompanying elements described in the present disclosure may be used for drainage from or introduction of fluids into other body cavities such as, by way of non-limiting example, veins, arteries, abdominal cavities, cranial cavities, etc.

The drainage tube 102 may include a proximal end 104 and a distal end 106. The drainage tube 102 may include at least one of an axial opening 108 in the distal end 106 and one or more lateral openings 110 proximate the distal end 106 into an open lumen of the drainage tube 102. The drainage device 100 may be configured to inhibit damage to the soft tissue surrounding the cavity while a portion of the drainage device 100 is inserted into the cavity or moved about within the cavity. For example, the distal end 106 of the drainage device 100 may include a substantially blunted geometry to prevent damage to the body cavity. In other words, the distal end 106 may not have any sharp, pointed, or abrupt edges that, if present, could puncture or otherwise damage soft tissue of a body cavity. In some embodiments, the drainage device 100 may include any and all of the features and characteristics of the drainage devices described in U.S. patent application Ser. No. 13/840,986, filed Mar. 15, 2013 and published as US 2013/0211385, now U.S. Pat. No. 8,940,713, issued Jan. 27, 2015, which is incorporated herein by reference for all that it discloses.

In some embodiments, the axial opening 108 and the one or more lateral openings 110 may have an average diameter that is substantially the same size or smaller than an average inside diameter of the drainage tube 102. Sizing the axial opening 108 and the one or more lateral openings 110 in this manner relative to the inside diameter of the drainage tube 102 may ensure that any clots (e.g., blood clots) suctioned into the drainage tube 102 are sufficiently small to pass through the drainage tube 102 without obstructing (e.g., clogging) the drainage tube 102.

The proximal end 104 of the drainage tube 102 may be coupled to an activation apparatus 112 that may include a control device 114. The control device 114 may be, for example, a knob configured to be manually manipulated (e.g., rotated) by a user, such as a practitioner, physician, nurse, patient, or care provider.

Figure 2:
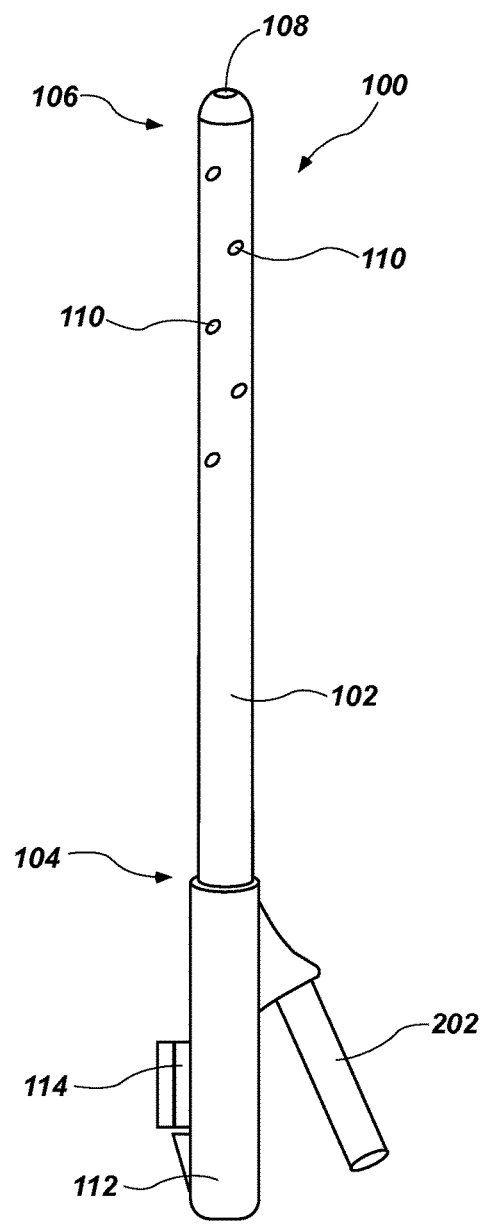
FIG. 2 shows a side view of the drainage device of FIG. 1.

FIG. 2 shows a side view of the drainage device 100 of FIG. 1. The drainage device 100 may include an fluid outlet 202 in fluid communication with the drainage tube 102 and may be configured for connection to a vacuum source for removal of material from a body cavity or to a source of one or more treatments to be introduced into the body cavity. In some embodiments, the fluid outlet 202 may be an integral extension of the drainage tube 102.

Figure 3:
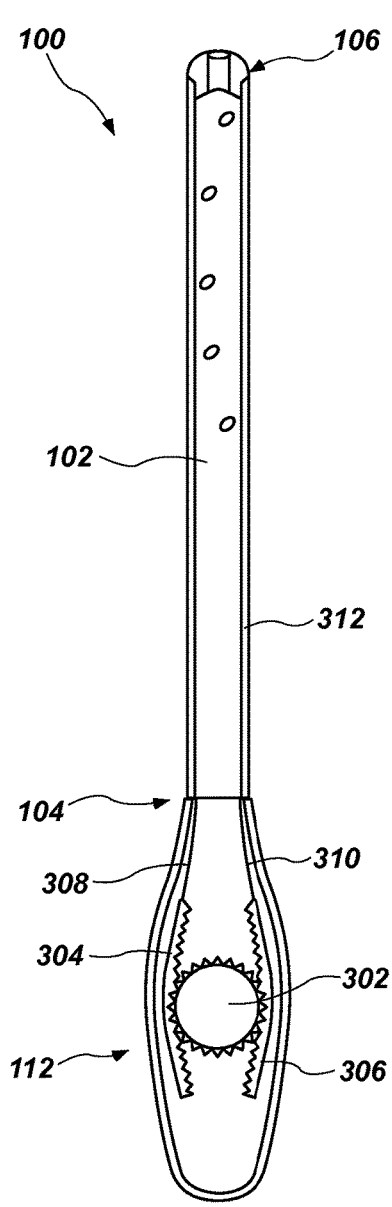
FIG. 3 shows a top cross-sectional view of the drainage device of FIG. 1.

FIG. 3 shows a cross-sectional view of the drainage device 100 of FIG. 1. An activation apparatus 112 may be attached at or near the proximal end 104 of the drainage tube 102. The activation apparatus 112 may include a pinion gear 302, a first rack 304, and a second rack 306. The first and second racks 304, 306 may be complementary to and meshed with the pinion gear 302. First and second flexible members 308, 310 may be attached to the first and second racks 304 and 306, respectively. The first and second flexible members 308, 310 may have an elongate shape and may include, for example, metallic wires made from steel, titanium, nitinol, or other metals or alloys. Additionally or alternatively, the first and second flexible members 308, 310 may include synthetic or natural fibers. As a further example, such wires or fibers may include a single strand or multiple strands of one or more materials bundled or woven together. The first and second flexible members 308, 310 may be disposed within closed lumens within a wall 312 of the drainage tube 102. The lumens through which the first and second flexible members 308, 310 extend may not be in fluid communication with the open lumen defined by the drainage tube 102 or with an exterior of the drainage tube 102. In some embodiments, the flexible members 308, 310 may be completely laterally enclosed within the wall 312 of the drainage tube 102. The lumens may be positioned within the wall of the drainage tube 102 such that each of the flexible members 308, 310 is substantially directly opposite the other across a diameter of the drainage tube 102.

Figure 4:
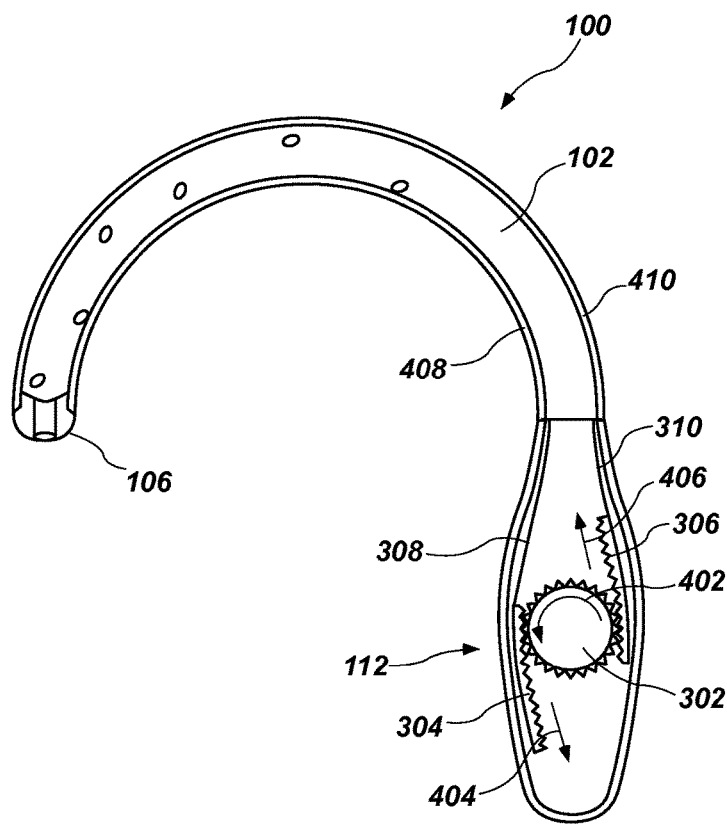
FIG. 4 shows a top cross-sectional view of the drainage device of FIG. 1 in a bent position.

FIG. 4 shows another cross-sectional view of the drainage device 100 of FIG. 1. The pinion gear 302 may rotate in response to an applied torque 402. As a non-limiting example, the torque 402 may be applied by a user manually operating the control device 114 (FIG. 1), which may be connected to the pinion gear 302. Other embodiments may include an automated system configured to operate the control device 114. Rotation of the pinion gear 302 may cause generally linear movement of the first rack 304 in a first direction 404 and a corresponding generally linear movement of the second rack 306 in a second, opposite direction 406. Movement of the first rack 304 may create tension in the first flexible member 308, which imparts a compressive force to a first side 408 of the drainage tube 102. Movement of the second rack 306 may allow slack in the second flexible member 310. The compressive force from the first flexible member 308 may cause the drainage tube 102 to contract along the first side 408 in which the first flexible member 308 is disposed and lengthen along a second side 410 in which the second flexible member 310 is disposed, causing the drainage tube 102 to assume an arcuate (e.g., bent) shape, such as the shape shown in FIG. 4. The magnitude of the applied torque 402 and the corresponding refraction of the first flexible member 308 may determine the extent of curvature imparted to the drainage tube 102. Torque may be applied in a direction opposite the direction indicated in FIG. 4, resulting in curvature of the drainage tube 102 in an opposite direction to the curvature shown. In some embodiments, the drainage device 100 may be configured such that the distal end 106 may rotate at least about 360° from a first fully curved position (e.g., pointing down and to the left in the perspective shown in FIG. 4) to a second, opposite fully curved position (e.g., pointing down and to the right from the same perspective).

In some embodiments, the drainage device 100 may include one or more optical fibers extending through lumens formed in the wall 312 of the drainage tube 102 and terminating at or near the distal end 106. Such optical fibers may be connected to a visualization device (e.g., a camera providing an image to an electronic display) to assist a user in placing or moving the drainage tube 102 within a patient's body cavity.

Figure 5:
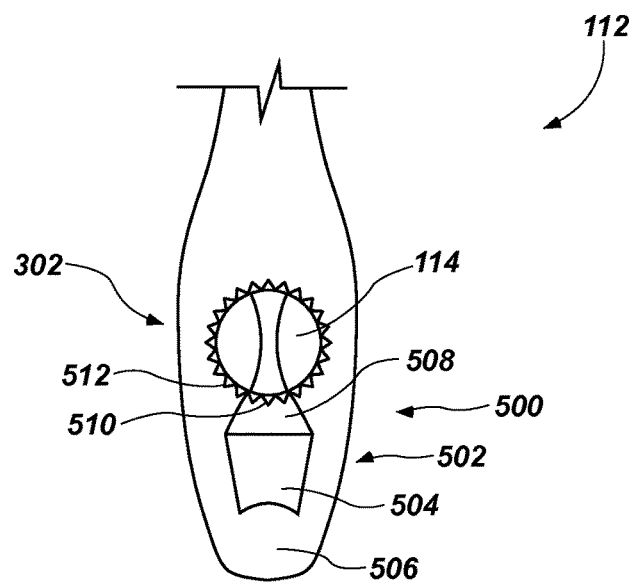
FIG. 5 shows an enlarged top view of an activation apparatus according to an embodiment of the present disclosure.

Referring now to FIG. 5, the activation apparatus 112 may include a compliant locking mechanism 500. The compliant locking mechanism 500 may have a locked position in which the compliant locking mechanism 500 maintains the control device 114 in a predetermined position selected by a user. The user may release (e.g., place the compliant locking mechanism 500 in an unlocked position) the compliant locking mechanism 500 to facilitate rotation of the control device 114. In some embodiments, the compliant locking mechanism 500 may be configured to allow rotation of the control device 114 under a sufficiently high applied torque 402 (FIG. 4) even when the compliant locking mechanism is in the locked position.

In some embodiments, the compliant locking mechanism 500 may include a lock lever 502 with a proximal end 504 pivotably affixed to a main housing portion 506 of the activation apparatus 112. As shown in FIG. 5, the proximal end 504 of the lock lever 502 may be resiliently (e.g., elastically) attached to the main housing portion 506. In some embodiments, the lock lever 502 may be integrally molded with the main housing portion 506 (e.g., by an injection molding process). In other words, the lock lever 502 may include a flexible structural portion (i.e., the resilient attachment of the proximal end 504 to the main housing portion 506) for rotating the lock lever 502 between the locked and unlocked positions. In other embodiments, the lock lever 502 may be attached to the main housing portion 506 with, e.g., a pinned hinge, and may be biased to a locked position by an elastic biasing element (e.g., a spring).

A distal end 508 of the lock lever 502 may include serrations (e.g., gear teeth) 510 configured to substantially mesh with gear teeth 512 of the pinion gear 302. In a locked position, the serrations 510 of the distal end 508 of the lock lever 502 may mesh with the gear teeth 512 of the pinion gear 302 and inhibit rotation of the pinion gear 302 when a torque is not applied (or an insufficient torque is applied) to the control device 114, thereby fixing the control device 114 at a desired position.

Figure 6:
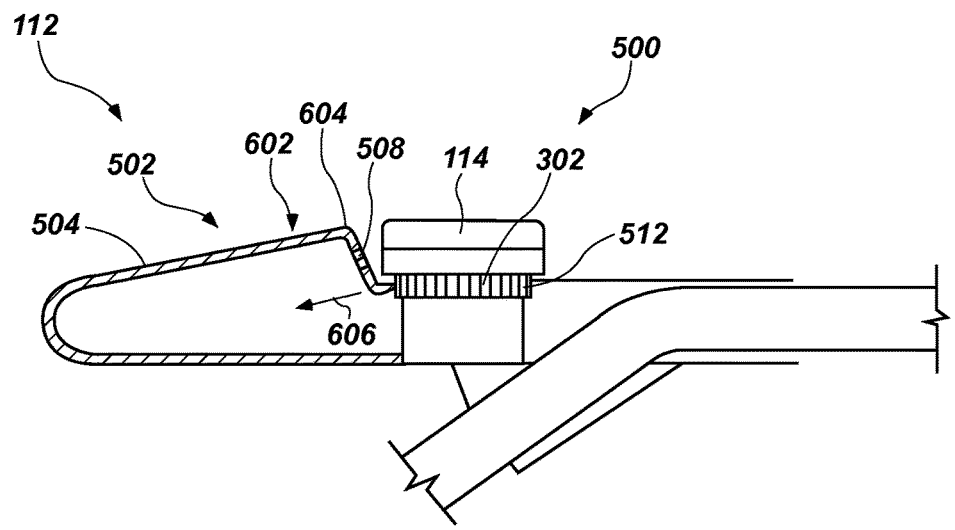
FIG. 6 shows a side cross-sectional view of the activation apparatus of FIG. 5.

When a user desires to unlock the compliant locking mechanism 500, the user may depress the lock lever 502 with a force 602, as shown in FIG. 6. The lock lever 502 may pivot at the proximal end 504, and the serrations 510 (FIG. 5) of the distal end 508 may move downward (with reference to the orientation of FIG. 6) to clear (i.e., disengage from) the gear teeth 512 of the pinion gear 302 and facilitate rotation of the control device 114 and pinion gear 302. The user may then rotate the control device 114 to the desired position and release the lock lever 502 to maintain the control device 114 in the selected position.

Alternatively, the user may leave the lock lever 502 in the locked position, and apply torque to the control device 114. At a sufficiently high torque value, the lock lever 502 may elastically deform at one or more locations, e.g., at an angled juncture 604. As torque is applied to the control device 114, mechanical interaction between the serrations 510 (FIG. 5) and the gear teeth 512 may force the distal end 508 of the lock lever 502 in direction 606, i.e., away from the pinion gear 302. Under a sufficiently high applied torque, the lock lever 502 may elastically deform enough to enable the serrations 510 (FIG. 5) to disengage from the gear teeth 512 of the pinion gear 302 and allow rotation of the pinion gear 302 even when the lock lever 502 remains in a locked position (i.e., in the absence of force 602). Thus, the compliant lock mechanism 500 may enable a user to adjust the position of the control device 114 without depressing the lock lever 502, while maintaining the position of the control device 114 in the absence of a sufficiently high applied torque.

For example, the compliant lock mechanism 500 may be configured such that it avoids or reduces movement of the control device 114 resulting from incidental contact when in the locked position, but allows movement at a threshold level of applied torque. Such a level of applied torque may be, by way of example and not limitation, a torque value of greater than about 0.5 lb·ft (0.68 N·m), greater than about 1.0 lb·ft (1.36 N·m), or greater than about 5.0 lb·ft (6.8 N·m).

Accordingly, a method of draining fluid from a body cavity may include positioning a distal end of a tube of a body cavity drainage device at a first position within the body cavity. Fluid may be drained from the body cavity through the distal end of the tube of the body cavity drainage device while the distal end of the tube is in the first position. A user may depress a locking lever to unlock a rotatable control device of the body cavity drainage device external to the body cavity. The user may move the distal end of the tube of the body cavity drainage device to a second, different position within the body cavity. Moving the distal end of the tube of the body cavity drainage device may include rotating the rotatable control device of the body cavity drainage device, and the rotatable control device may be coupled to the distal end of the tube of the body cavity drainage device by flexible members.

In some embodiments, a drainage device may include a fluid outlet that is substantially aligned with the drainage tube. For example, referring now to FIG. 7, a schematic side view of another embodiment of a drainage device 700 is shown. In this embodiment, a drainage tube 702 extends along a central axis $A_c$, through an activation apparatus 704, and to a fluid outlet 706 also aligned along the central axis $A_c$. In some embodiments, a single tube extending through the activation apparatus 704 may form the drainage tube 702 and the fluid outlet 706. In other words, the drainage device 700 may comprise a unitary drainage tube 702 with a distal end 708 for insertion into a body cavity of a patient, a proximal end 710 including a fluid outlet 706, and an activation apparatus 704 disposed on the drainage tube 702 between the proximal end 710 and the distal end 708. In other embodiments, the drainage tube 702 and the fluid outlet 706 may be two separate tubes coupled (e.g., bonded, press-fit, glued) together.

Figure 7:
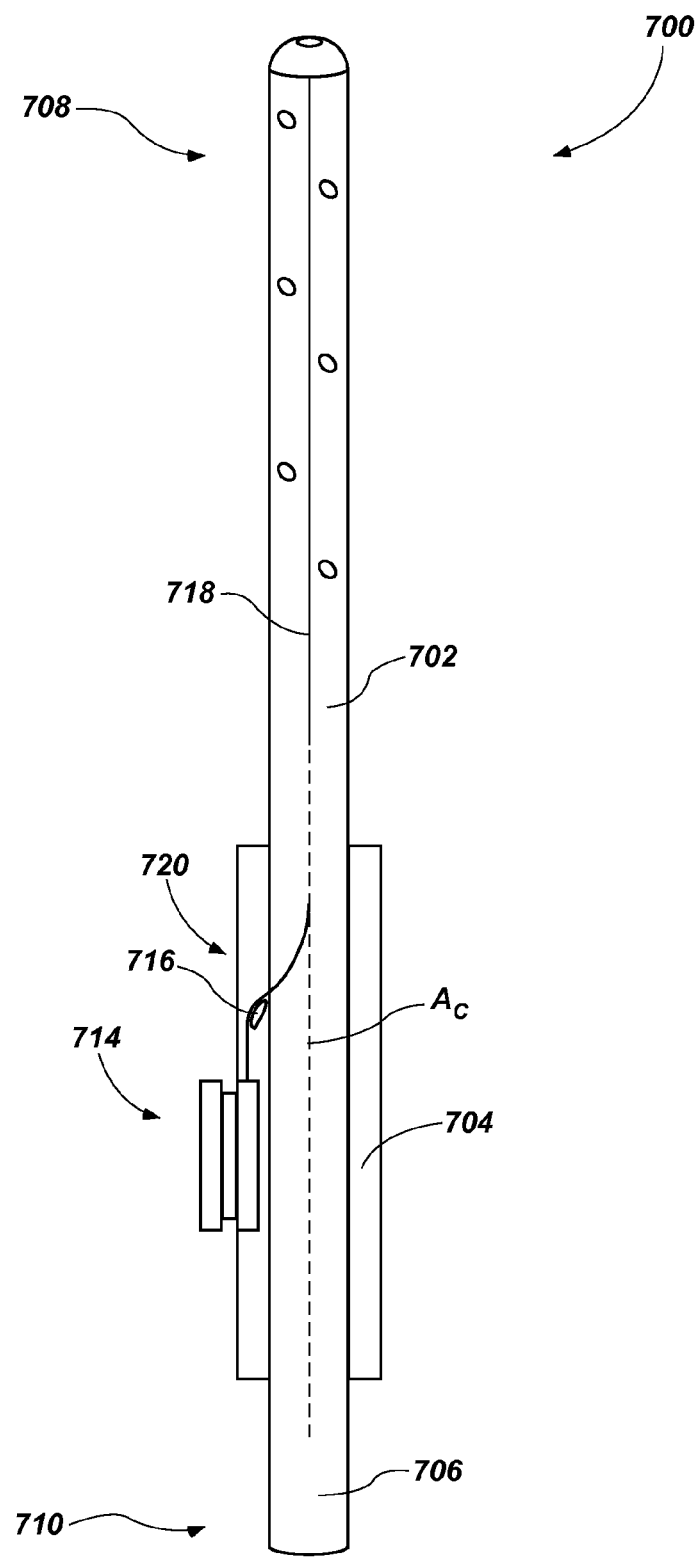
FIG. 7 shows a schematic side view of a drainage device according to an embodiment of the present disclosure.

In the embodiment of FIG. 7, a control device 714 may be disposed in a position offset from a central axis $A_c$ of the drainage tube 702. At least one flexible member 718, substantially as described above in connection with FIGS. 3 and 4, may extend from the control device 714 along an at least partially curvilinear (i.e., arcuate) path 720. The at least one flexible member 718 may be constrained to the curvilinear path 720 by guides 716 in the activation apparatus 704 and channels in the drainage tube 702. The control device 714, the at least one flexible member 718, and the drainage tube 702 may function in a similar manner to that described above in connection with FIGS. 3 and 4. The activation apparatus 704 may further include a compliant locking mechanism, as described above in connection with FIGS. 5 and 6.

Figure 8:
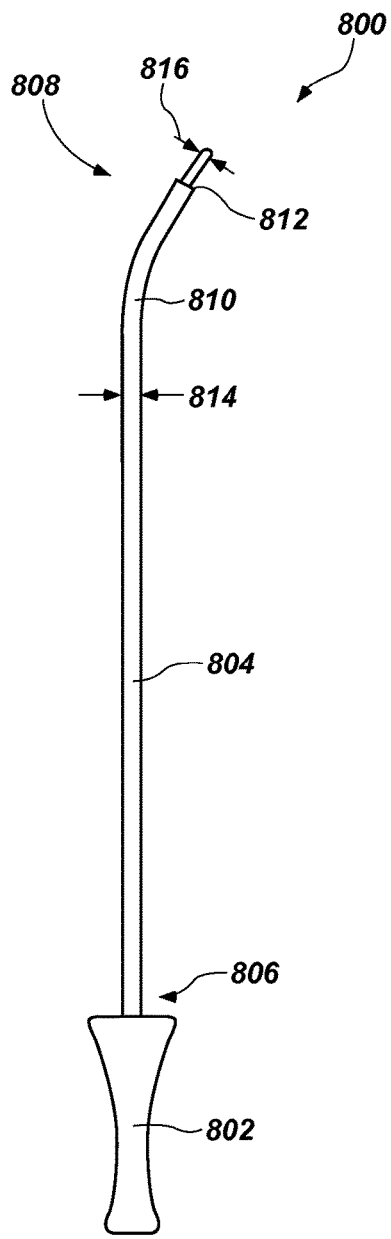
FIG. 8 shows a side view of a drainage tube placement tool according to an embodiment of the present disclosure.

Referring now to FIG. 8, a side view of a drainage tube placement tool 800 is shown. The drainage tube placement tool 800 may include a handle 802 affixed to a shaft 804 at a proximal end 806. The shaft 804 may be substantially straight, or may include a curved portion 810 near a distal end 808, as shown in FIG. 8. In some embodiments, the shaft 804 may have a substantially circular cross-sectional shape. In other embodiments, the shaft 804 may have a different cross-sectional shape, such as an elliptical shape, a rectilinear shape, or combinations thereof.

The shaft 804 may include a shoulder 812 (e.g., a step) where the cross-sectional shape of the shaft 804 varies from a first diameter 814 to a second, smaller diameter 816. As shown in FIG. 8, the shoulder 812 may be disposed proximate the distal end 808 of the shaft 804. By way of example and not limitation, the shoulder 812 may be positioned within about one (1) inch (25.4 mm) or less of the distal end 808 of the shaft 804. In other embodiments (e.g., as shown below in FIG. 10), the shoulder may be disposed proximate the handle portion 802, or the drainage tube placement tool 800 may not include a shoulder.

Figure 9:
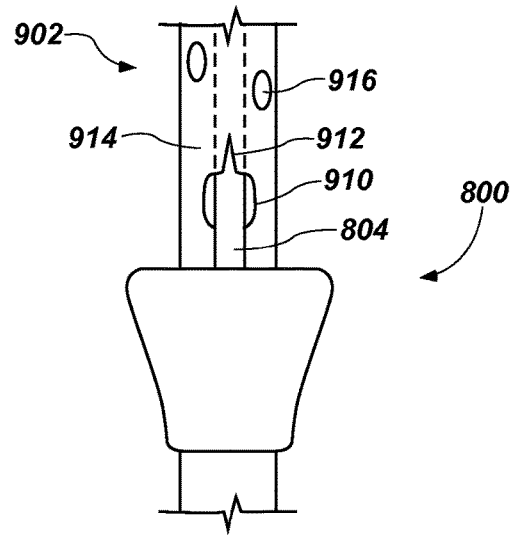
FIG. 9 shows a detail view of the drainage tube placement tool of FIG. 8 disposed within a drainage tube.

Referring now to FIG. 9, a user may insert the shaft 804 of the drainage tube placement tool 800 through a lateral opening 910 of a drainage tube 902. The lateral opening 910 may be similar to the lateral openings 110 described in connection with FIGS. 1 and 2. In some embodiments, the lateral opening 910 may include features configured to facilitate insertion of the drainage tube placement tool 800 within the drainage tube 902. For example, a slit 912 may extend from a periphery of the lateral opening 910 into a wall 914 of the drainage tube 902. Upon insertion of the distal end 812 (FIG. 8) of the drainage tube placement tool 800 within the lateral opening 910, the slit 912 may at least partially open, as shown in FIG. 9, to ease passage of the drainage tube placement tool 800 through the drainage tube 902. Upon removal of the drainage tube placement tool 800 from the drainage tube 902, the slit 912 may substantially close, and the diameter of the lateral opening 910 may be substantially similar to the diameter of other lateral openings 916. Suction applied to the drainage tube 902 after removal of the drainage tube placement tool 800 may also assist the slit 912 to close. In other embodiments, the diameter of the lateral opening 910 may be greater than the diameter of other lateral openings 110.

Figure 10:
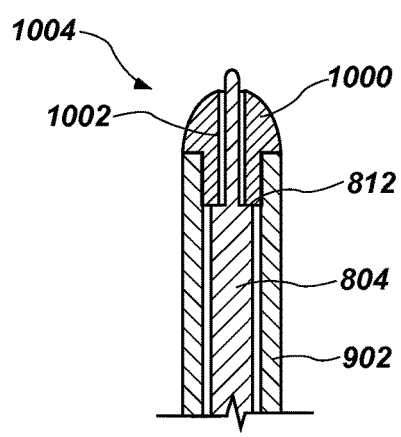
FIG. 10 shows a cross-sectional detail view of the drainage tube placement tool of FIG. 8 disposed within a drainage tube.

The drainage tube placement tool 800 may be configured to stop at a predetermined insertion distance within the drainage tube 902. Referring now to FIG. 10, after the drainage tube placement tool 800 (FIG. 8) is inserted into the lateral opening 910 (FIG. 9) of the drainage tube 902, the user may continue to insert the drainage tube placement tool 800 within the drainage tube 902 until the shoulder 812 of the shaft 804 of the drainage tube placement tool 800 abuts a ferrule 1000 disposed near the distal end 1004 of the drainage tube 902 and the shoulder 812 prevents further insertion of the placement tool 800 within the drainage tube 902. The portion of the shaft 804 having the second diameter 816 (FIG. 8) may enter an axial opening 1002 of the ferrule 1000. In this position, the distal end 808 (FIG. 8) of the drainage tube placement tool 800 may be disposed proximate the distal end 1004 of the drainage tube 902. In some embodiments, the axial opening 1002 of the ferrule 1000 may have a diameter smaller than an inside diameter of the drainage tube 902.

In some embodiments, the shaft 804 of the drainage tube placement tool 800 may have a length sufficient to extend through the lateral opening 910 of the body cavity drainage tube 902, through a central lumen of the body cavity drainage tube 902, and position the distal end 808 of the shaft 804 past the distal end 1004 of the drainage tube 902. In other words, when the shaft 804 is inserted fully into the body cavity drainage tube 902, the distal end 808 of the shaft 804 may protrude beyond the distal end 1004 of the drainage tube 902.

In some embodiments, at least one of the flexible members 308, 310 (FIG. 3) or 718 (FIG. 7) may be attached to the ferrule 1000. In other words, the ferrule 1000 may be coupled to a control device (e.g., control device 114 (FIGS. 1 and 2) or control device 714 (FIG. 7)) of an activation apparatus (e.g., activation apparatus 112 (FIG. 3) or activation apparatus 704 (FIG. 7)) through one or more flexible members 308, 310, and 718.

The drainage tube placement tool 800 may contribute additional stiffness (i.e., rigidity) to the drainage tube 902 to enable a user to insert the drainage tube 902 through an incision in a patient's body and into, e.g., the pleural cavity, without collapsing (e.g., kinking) the drainage tube 902. In some embodiments, the drainage tube placement tool 800 may be made from a material having a greater modulus of elasticity (i.e., a greater stiffness) than the material of the drainage tube 902.

In use, a user may insert the distal end 808 of the drainage tube placement tool 800 into the drainage tube 902, grasp the handle 802, and insert the drainage tube 902 with the drainage tube placement tool 800 disposed therein through an incision and into the body cavity. The user may then remove the drainage tube placement tool 800 from the drainage tube 902, leaving at least a portion of the drainage tube 902 disposed within the body cavity.

The curved portion 810 of the drainage tube placement tool 800 may be shaped to ease insertion of the drainage tube 902 with the drainage tube placement tool 800 disposed therein within a body cavity of a particular configuration. For example, the curved portion 810 of the drainage tube placement tool 800 may have a shape of a desired path the drainage tube 902 may follow as the drainage tube 902 is inserted into a body cavity. By way of another example, the curve may facilitate directing the placement of the drainage tube 902 within the body cavity.

Figure 11:
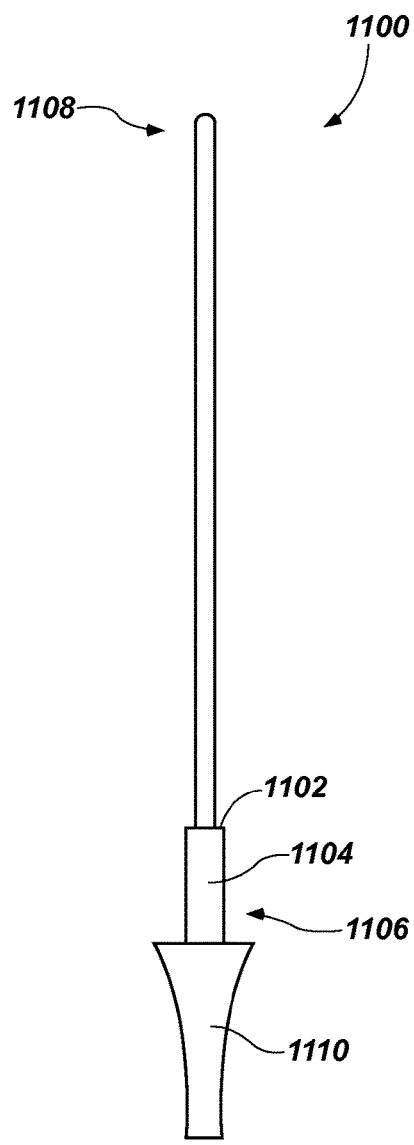
FIG. 11 shows a side view of a drainage tube placement tool according to another embodiment of the present disclosure.

Referring now to FIG. 11, another embodiment of a drainage tube placement tool 1100 is shown. The drainage tube placement tool 1100 may include a shaft 1104 with a shoulder 1102 disposed near a proximal end 1106 of the shaft 1104. A distal end 1108 of the shaft 1104 may be inserted in a lateral opening 910, 916 (FIG. 9) of a drainage tube 902. The shoulder 1102 may abut a wall 914 (FIG. 9) of the drainage tube 902 surrounding the lateral opening 910, 916 at a predetermined insertion distance. In other embodiments, the shoulder 1102 may be absent, and a handle 1110 may abut against the lateral opening 910, 916 to stop further insertion of the drainage tube placement tool 1100 into a drainage tube. Thus, the drainage tube placement tool 1100 may be used with a drainage tube device that does or does not include a ferrule 1000 (FIG. 10). For example, the drainage tube placement tool 1100 may be used with a drainage device according to the present disclosure, e.g., drainage devices 100, 700, or may be used with prior art drainage devices. As shown in FIG. 11, the shaft 1104 of the drainage tube placement tool 1100 may be substantially straight. In other embodiments, the shaft 1104 of the drainage tube placement tool 1100 may include a curved portion 810 like that shown in the embodiment of FIG. 8.

In some embodiments, the shaft 804, 1104 of the drainage tube placement tool 800, 1100 may be hollow (e.g., may include a channel therethrough) to accommodate a guide wire for aiding placement of the drainage tube within a body cavity and/or to accommodate one or more optical fibers therein. A guide wire may be placed in a desired location through a hollow needle, and one or more dilators may be threaded over the guide wire to expand an incision made by the hollow needle through the skin and/or other tissue. When the incision is sufficiently expanded, the drainage tube placement tool 800, 1100 may be inserted into a drainage tube 102, 702 as described above, and the guide wire may be threaded through the drainage tube placement tool 800, 1100. A distal end of the drainage tube 102, 702 may then be placed in the body cavity through the expanded incision using the guide wire. In some embodiments, one or more optical fibers may be inserted through the channel of the drainage tube placement tool 800, 1100. The one or more optical fibers may be connected to a visualization device (e.g., a camera in communication with an electronic display) to assist the user in placing a drainage tube 102, 702 within the body cavity.

Figure 12:
FIG. 12 shows a side view of a cleaning device for a drainage tube according to an embodiment of the present disclosure.

FIG. 12 shows an embodiment of a cleaning device 1200 according to the present disclosure. The cleaning device 1200 may include a handle 1202, a shaft 1204, and a cleaning instrument 1206. The cleaning instrument 1206 may be configured to be inserted through an fluid outlet 202, 704 (FIGS. 2 and 7) of the drainage device 100, 700. In some embodiments, the cleaning instrument 1206 may be inserted into the drainage device 100, 700 while a portion of the drainage tube 102 remains disposed within a body cavity. The cleaning instrument 1206 may be configured to retrieve solid matter, e.g., blood clots or other coagulations of physiological fluids, from the drainage tube 102. In use, a user may remove a vacuum source from the fluid outlet 202, 704 of the drainage device 100, 700. The user may then insert the cleaning instrument 1206 into the fluid outlet 202, 704, grasp the handle 1202, and feed the cleaning device 1200 into the drainage tube 102 until the cleaning instrument 1206 contacts the solid matter. The user may remove the cleaning device 1200 and solid matter from the drainage tube 102 and reconnect the vacuum source to the fluid outlet 202, 704. In some embodiments, the cleaning instrument 1206 may comprise a coil of resilient material, such as a metal alloy or a polymer. The cleaning instrument 1206 may have a helical shape, which may be rotated within the drainage tube 102 to force the solid matter out of the drainage tube 102.

Figure 13:
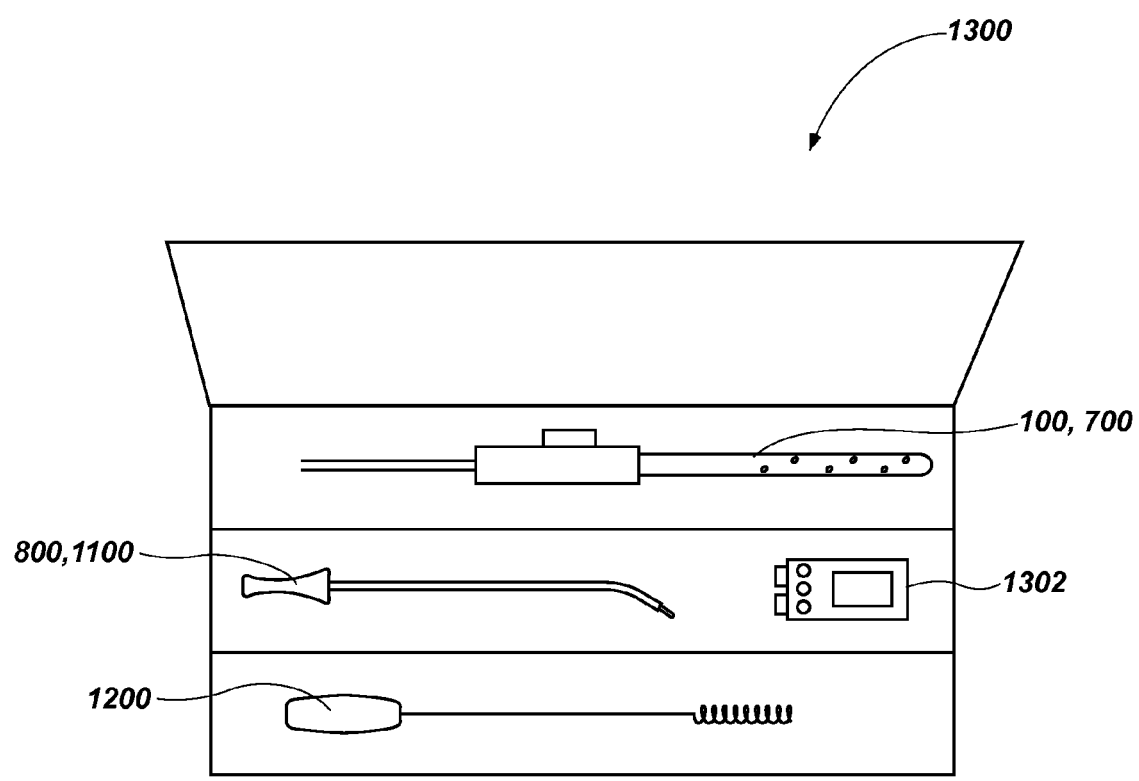
FIG. 13 shows a top view of a surgical kit including a drainage device and a drainage tube placement tool according to an embodiment of the present disclosure.

Referring to FIG. 13, a surgical kit 1300 may include at least a drainage device 100, 700 and a drainage tube placement tool 800, 1100. Each of the drainage device 100, 700 and the drainage tube placement tool 800, 1100 in the surgical kit 1300 may be substantially as described above. In some embodiments, the surgical kit 1300 may also include one or more of a cleaning device 1200 for removal of obstructions in the drainage device 100, 700, a guide wire to facilitate placement of the drainage device 100, 700, at least one dilator for expanding an incision to facilitate placement of the drainage device 100, 700, and a visualization device 1302 to facilitate placement of the drainage device 100, 700. The visualization device 1302 may include, for example, a fiber optic scope and/or a camera. The elements in the surgical kit 1300 may provide complementary tools for a surgeon or other practitioner to use for draining a patient's body cavity. Each of the elements in the surgical kit 1300 or portions thereof may be sterilized and otherwise prepared for use in surgery. In addition, one or more of the elements in the surgical kit 1300 may be provided at least partially within a sterile envelope, protective covering, enclosure, or other container within the surgical kit 1300 for additional protection from contamination or damage.

Figure 14:
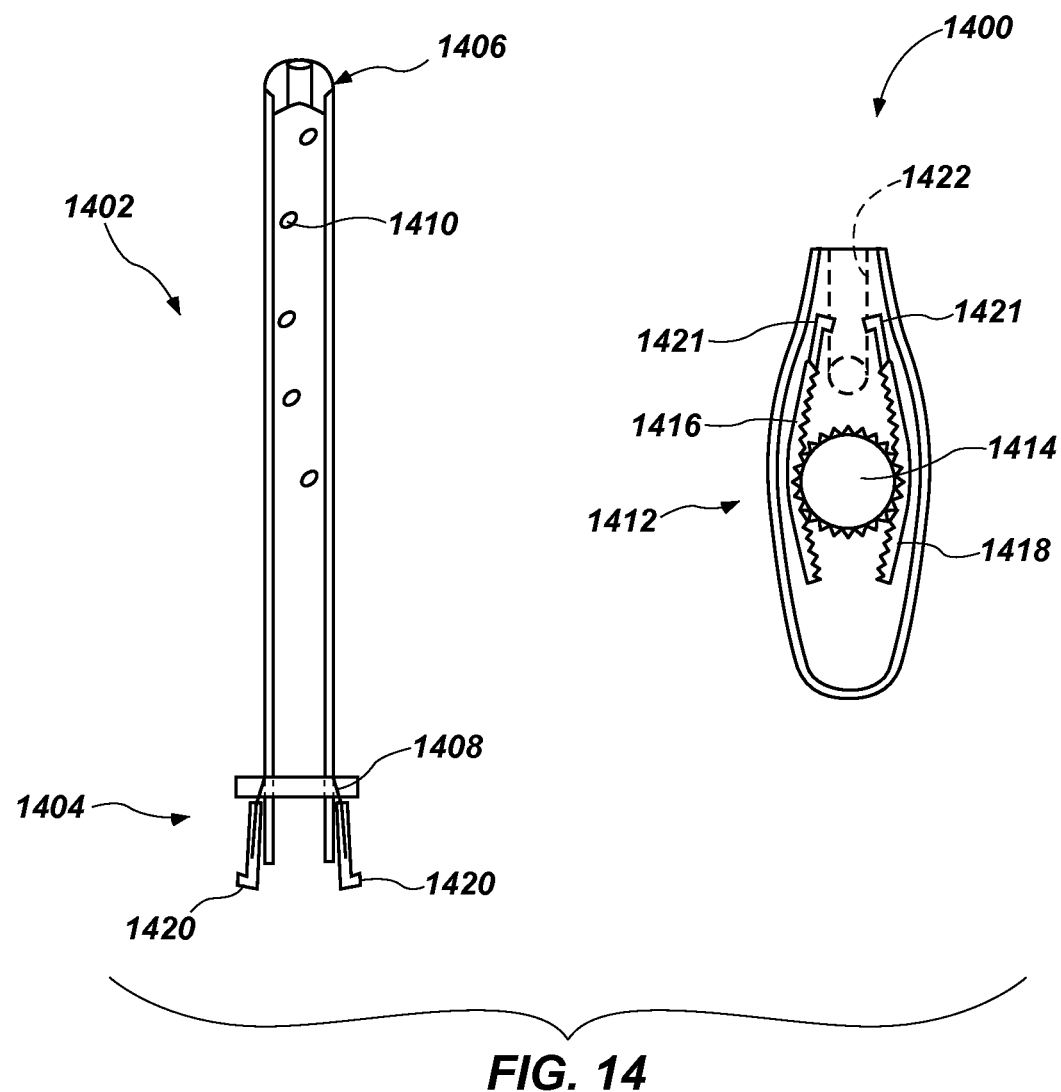
FIG. 14 shows a cross-sectional view of a drainage device according to an embodiment of the present disclosure.

FIG. 14 illustrates an embodiment of a drainage device 1400 including an activation apparatus 1412 and a detachable drainage tube 1402. The activation apparatus 1412 and detachable drainage tube 1402 may be configured to be detachably coupled together for positioning the detachable drainage tube 1402 in a body cavity (e.g., for initial insertion and/or for repositioning within the body cavity). The activation apparatus 1412 and detachable drainage tube 1402 may be selectively detached from each other, such as to provide increased mobility to a patient. The detachable drainage tube 1402 may include at least some similar features as the drainage tube 102 described above. For example, the detachable drainage tube 1402 may include a proximal end 1404, a distal end 1406, and one or more lateral openings 1410 proximate the distal end 1406 of the detachable drainage tube 1402. The detachable drainage tube 1402 may also include elongated flexible members 1408 extending from the proximal end 1404 to at or near the distal end 1406 of the detachable drainage tube 1402, which may be disposed within lumens longitudinally extending through a sidewall of the detachable drainage tube 1402.

The activation apparatus 1412 may include at least some similar features as the activation apparatus 112 described above. For example, the activation apparatus 1412 may include a control device 1414, such as a knob or other element configured to be manually manipulated (e.g., rotated) by a user to remotely move the distal end 1406 of the detachable drainage tube 1402 when coupled thereto. The control device 1414 may include a pinion configured to engage with first and second racks 1416, 1418.

The proximal end 1404 of the detachable drainage tube 1402 may be configured to couple the detachable drainage tube 1402 to the activation apparatus 1412, and the activation apparatus 1412 may be configured to couple with the detachable drainage tube 1402 in a complementary fashion. Additionally, a linking element 1420 may be coupled to a proximal end of each of the elongated flexible members 1408 for operably connecting each of the elongated flexible members 1408 to a respective one of the first and second racks 1416, 1418. By way of example and not limitation, each linking element 1420 may include a hook and each of the first and second racks 1416, 1418 may include a complementary slot or hook 1421. When operably connected, the hook of the linking element 1420 may latch onto the complementary slot or hook 1421 of the respective one of the first and second racks 1416, 1418. By way of another example, the linking element 1420 may include a notch (e.g., an annular notch) and each of the first and second racks 1416, 1418 may include a complementary ridge or O-ring configured to deflect and snap into the notch of the linking element 1420 when the detachable drainage tube 1402 is operably connected to the activation apparatus 1412.

The activation apparatus 1412 may include a suction tube 1422 that may be configured to form a fluid seal with a proximal end of the detachable drainage tube 1402 when the detachable drainage tube 1402 is operably connected to the activation apparatus 1412. Accordingly, suction may be applied to the suction tube 1422 to draw fluids from a body cavity through the detachable drainage tube 1402.

Accordingly, the drainage device 1400 may be used to withdraw fluids from a body cavity of a patient by inserting the distal end 1406 of the detachable drainage tube 1402 into the body cavity and, prior to or after insertion of the distal end 1406 of the detachable drainage tube 1402, operably coupling the activation apparatus 1412 to the proximal end 1404 of the detachable drainage tube 1402. To operably couple the activation apparatus 1412 to the detachable drainage tube 1402, a fluid seal may be formed between the detachable drainage tube 1402 and the suction tube 1422 and the linking elements 1420 may be coupled to the first and second racks 1416, 1418. When operably connected, the activation apparatus 1412 may be used to remotely position the distal end 1406 of the detachable drainage tube 1402 within the body cavity.

The activation apparatus 1412 may also be detached from the detachable drainage tube 1402, such as to enable increased patient mobility. For example, the linking elements 1420 may be decoupled from the first and second racks 1416, 1418, and the detachable drainage tube 1402 may be decoupled from the suction tube 1422. In some embodiments, after the activation apparatus 1412 is detached from the detachable drainage tube 1402, the proximal end of the detachable drainage tube 1402 may be capped or plugged to inhibit fluid from inadvertently draining out of the detachable drainage tube 1402.

Referring to FIG. 14 in conjunction with FIG. 13, the surgical kit 1300 may, in some embodiments, include the drainage device 1400 in a detached or an attached configuration. In some embodiments, more than one detachable drainage tube 1402, such as identical detachable drainage tubes 1402 or detachable drainage tubes 1402 of different lengths, diameters, materials, stiffnesses, etc., may be included in the surgical kit 1300.

While the disclosure may be susceptible to various modifications and alternative forms, specific embodiments have been shown by way of example in the drawings and have been described in detail herein. However, it should be understood that the disclosure is not intended to be limited to the particular forms disclosed. Additionally, embodiments and features of the disclosure shown and/or described separately may be combined.

What is claimed is:

1. A body cavity drainage device for a patient, comprising:
   a drainage tube having a proximal end, a distal end, and one or more lumens extending longitudinally through a wall thereof, the distal end configured to be inserted into a body cavity of a patient to facilitate use of the body cavity drainage device; and
   an activation apparatus configured to alter a position of the distal end of the drainage tube relative to the proximal end of the drainage tube, the activation apparatus comprising:
     a housing portion;
     a rotatable control device rotatably coupled to the housing portion;
     one or more elongated flexible members disposed within the one or more lumens extending longitudinally through a wall of the drainage tube, the one or more flexible members operably coupled to the rotatable control device at a proximal end of the one or more flexible members and to the drainage tube at or near a distal end of the one or more flexible members; and
     a compliant locking mechanism configured to maintain an angular position of the rotatable control device when in a locked position and in the absence of a torque applied to the rotatable control device, and to allow rotation of the control device when in an unlocked position upon application of a torque to the rotatable control device, the compliant locking mechanism comprising:
       a locking lever having a distal end configured to engage with the rotatable control device in the locked position, and having a proximal end resiliently attached to the housing portion for rotating between the locked position and the unlocked position, wherein the distal end of the locking lever has a concave profile matching a convex profile of the rotatable control device.

2. The body cavity drainage device of claim 1, wherein the compliant locking mechanism is configured to allow rotation of the control device when in the locked position upon application of torque of a predetermined value to the control device.

3. The body cavity drainage device of claim 2, wherein the torque of a predetermined value is a torque of at least about 1 lb·ft (1.36 N·m).

4. The body cavity drainage device of claim 1, wherein the proximal end of the locking lever is integrally molded with the housing portion.

5. The body cavity drainage device of claim 1, wherein the locking lever is biased to the locked position.

6. The body cavity drainage device of claim 1, wherein the locking lever comprises a flexible structural portion configured to be manually depressed by a user.

7. The body cavity drainage device of claim 1, wherein the locking lever is configured to move from the locked position to the unlocked position upon being manually depressed.

8. The body cavity drainage device of claim 1, wherein the distal end of the locking lever comprises serrations.

9. The body cavity drainage device of claim 8, wherein the control device comprises a pinion gear, and wherein the serrations of the locking lever are configured to engage with gear teeth of the pinion gear when the compliant locking mechanism is in the locked position.

10. The body cavity drainage device of claim 9, wherein the serrations of the locking lever are configured to disengage from the gear teeth of the pinion gear when the locking lever is in the unlocked position.

11. The body cavity drainage device of claim 8, wherein the locking lever comprises a compliant portion proximate the distal end of the locking lever.

12. The body cavity drainage device of claim 11, wherein the compliant portion comprises an angled juncture between two portions of the locking lever.

13. A body cavity drainage device for a patient, comprising:
   a drainage tube having a proximal end and a distal end; and
   an activation apparatus coupled to the proximal end of the drainage tube, the activation apparatus comprising:
      a pinion gear attached to a control device;
      at least one rack configured to mesh with the pinion gear;
      at least one flexible member extending along a length of the drainage tube and coupled to the distal end of the drainage tube, the at least one flexible member attached to the at least one rack; and
      a compliant locking mechanism proximate the control device, the compliant locking mechanism comprising a resilient locking lever configured to resiliently rotate between a locked position and an unlocked position and serrations configured to engage with gear teeth of the pinion gear when the locking lever is in the locked position, wherein the locking lever is located outside of a profile of the pinion gear.

14. The body cavity drainage device of claim 13, wherein the at least one rack configured to mesh with the pinion gear comprises two racks configured to mesh with the pinion gear, and wherein the at least one flexible member comprises two flexible members, each of the two flexible members attached to a respective rack of the two racks.

15. The body cavity drainage device of claim 13, wherein the serrations of the compliant locking mechanism are configured to disengage from the gear teeth of the pinion gear upon application of a torque of at least a predetermined value to the control device.

16. A method of forming a body cavity drainage device for a patient, comprising:
   coupling an activation apparatus to a proximal end of a drainage tube, the activation apparatus configured to bend the drainage tube in response to a torque input at a rotatable control device of the activation apparatus;
   forming a locking mechanism by resiliently coupling a proximal end of a locking lever to a housing of the activation apparatus; and
   engaging a concave distal end of the locking lever with a convex outer profile of the rotatable control device to substantially prevent rotation of the rotatable control device in the absence of an applied torque to the rotatable control device.

17. The method of claim 16, wherein resiliently coupling a proximal end of a locking lever to a housing of the activation apparatus comprises providing clearance sufficient to enable the locking lever to resiliently move between an unlocked position and a locked position in which free rotation of the control device is allowed.

18. The method of claim 16, wherein engaging a distal end of the locking lever with the rotatable control device comprises compliantly engaging the distal end of the locking lever with the rotatable control device to allow rotation of the rotatable control device when the locking mechanism is in a locked position and torque of a predetermined value is applied to the rotatable control device.

19. A method of draining fluid from a body cavity, comprising:
   positioning a distal end of a tube of a body cavity drainage device at a first position within the body cavity;
   engaging a concave distal end of a locking lever resiliently coupled to a housing of an activation apparatus at a proximal end of the locking lever with an outer surface of a rotatable control device of the body cavity drainage device external to the body cavity to lock the rotatable control device in position;
   draining fluid from the body cavity through the distal end of the tube of the body cavity drainage device in the first position;
   depressing the locking lever to rotate the concave distal end of the locking lever away from engagement with the rotatable control device of the body cavity drainage device to unlock the rotatable control device; and
   moving the distal end of the tube of the body cavity drainage device to a second, different position within the body cavity, comprising:
      rotating the rotatable control device of the body cavity drainage device, the rotatable control device being coupled to the distal end of the tube of the body cavity drainage device by flexible members.

* * * * *